(12) United States Patent
Smith et al.

(10) Patent No.: US 7,903,240 B2
(45) Date of Patent: *Mar. 8, 2011

(54) OPTICAL SENSING DEVICE

(75) Inventors: Terry L. Smith, Roseville, MN (US); Yasha Yi, Woodbury, MN (US); Barry J. Koch, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 331 days.

This patent is subject to a terminal disclaimer.

(21) Appl. No.: 11/565,920

(22) Filed: Dec. 1, 2006

(65) Prior Publication Data
US 2008/0291446 A1 Nov. 27, 2008

(51) Int. Cl.
G01B 9/02 (2006.01)
G02B 6/26 (2006.01)
G01N 21/00 (2006.01)

(52) U.S. Cl. .................. 356/39; 356/337; 356/480

(58) Field of Classification Search .................. 356/436, 356/440, 442, 337, 338; 385/28, 30, 39, 385/15; 372/98, 108
See application file for complete search history.

(56) References Cited

U.S. PATENT DOCUMENTS

| | | |
|---|---|---|
| 4,185,257 A | 1/1980 | Nakajima |
| 4,775,214 A | 10/1988 | Johnson |
| 5,398,256 A | 3/1995 | Hohimer et al. |
| 5,420,880 A | 5/1995 | Tabatabaie et al. |
| 5,537,432 A | 7/1996 | Mehuys et al. |
| 5,651,018 A | 7/1997 | Mehuys et al. |
| 5,748,663 A | 5/1998 | Chenausky |
| 5,910,963 A | 6/1999 | Simon |
| 6,009,115 A | 12/1999 | Ho |
| 6,286,262 B1 | 9/2001 | Prevot et al. |
| 6,490,039 B2 | 12/2002 | Maleki et al. |
| 6,515,749 B2 | 2/2003 | Pipino |
| 6,580,851 B1 | 6/2003 | Vahala et al. |
| 6,583,399 B1 | 6/2003 | Hunziker et al. |
| 6,608,716 B1 | 8/2003 | Armstrong et al. |
| 6,657,731 B2 | 12/2003 | Tapalian et al. |
| 6,661,950 B1 | 12/2003 | Strecker |
| 6,680,962 B2 | 1/2004 | Liu et al. |
| 6,711,200 B1 | 3/2004 | Scherer et al. |
| 6,741,628 B2 | 5/2004 | Painter et al. |
| 6,751,368 B2 | 6/2004 | Lim et al. |

(Continued)

FOREIGN PATENT DOCUMENTS

WO WO 98/53535 11/1998

(Continued)

OTHER PUBLICATIONS

Brun et al., "Coupling nanocrystals to a high-Q silica microsphere: Entanglement in quantum dots via photon exchange," *Physical Review A*, vol. 61, pp. 032307-1-032307-5 (2000).

(Continued)

*Primary Examiner* — Hwa S. A Lee
(74) *Attorney, Agent, or Firm* — Kristofor L. Storvick

(57) ABSTRACT

An optical sensing system and method are disclosed. The optical sensing system includes one or more bus waveguides. A first bus waveguide includes an input port that is in optical communication with a light source. The system further includes a microresonator optically coupled to the bus waveguides and an optical scattering center configured for alteration of a strength of optical coupling between the optical scattering center and the microresonator. In addition, the system includes a detector in optical communication one of the bus waveguides or the microresonator.

47 Claims, 8 Drawing Sheets

U.S. PATENT DOCUMENTS

| | | |
|---|---|---|
| 6,772,480 B2 | 8/2004 | Prevot et al. |
| 6,781,690 B2 | 8/2004 | Armstrong et al. |
| 6,795,481 B2 | 9/2004 | Maleki et al. |
| 6,876,796 B2 | 4/2005 | Garito et al. |
| 6,888,987 B2 | 5/2005 | Sercel et al. |
| 6,901,101 B2 | 5/2005 | Frick |
| 6,947,632 B2 | 9/2005 | Fischer et al. |
| 7,062,131 B2 | 6/2006 | Ilchenko |
| 7,085,452 B1 | 8/2006 | Lin et al. |
| 7,228,016 B2 | 6/2007 | Beausoleil |
| 7,271,379 B2 | 9/2007 | Fan et al. |
| 7,292,112 B2 | 11/2007 | Oxborrow |
| 7,389,025 B2 | 6/2008 | Smith et al. |
| 7,486,855 B2 | 2/2009 | Smith et al. |
| 7,512,298 B2 | 3/2009 | Yi et al. |
| 7,665,891 B1 | 2/2010 | Savchenkov et al. |
| 2002/0122179 A1 | 9/2002 | Pipino |
| 2003/0063426 A1 | 4/2003 | Smirnov et al. |
| 2003/0202555 A1 | 10/2003 | Liu et al. |
| 2003/0231826 A1 | 12/2003 | Boyd et al. |
| 2004/0023396 A1 | 2/2004 | Boyd et al. |
| 2004/0137478 A1 | 7/2004 | Arnold et al. |
| 2004/0247008 A1 | 12/2004 | Scheuer et al. |
| 2005/0003520 A1 | 1/2005 | Misiakos et al. |
| 2005/0013529 A1 | 1/2005 | Chiu et al. |
| 2005/0018274 A1 | 1/2005 | Halas et al. |
| 2005/0077513 A1 | 4/2005 | Fan et al. |
| 2005/0078731 A1 | 4/2005 | Fan et al. |
| 2005/0141809 A1 | 6/2005 | Gardner et al. |
| 2005/0210989 A1 | 9/2005 | Ja et al. |
| 2005/0226564 A1 | 10/2005 | Gardner et al. |
| 2005/0263679 A1 | 12/2005 | Fan et al. |
| 2005/0286602 A1 | 12/2005 | Gunn et al. |
| 2006/0062508 A1 | 3/2006 | Guo et al. |
| 2006/0170931 A1 | 8/2006 | Guo et al. |
| 2007/0001773 A1 | 1/2007 | Oxborrow |
| 2007/0147445 A1 | 6/2007 | Ishaaya et al. |
| 2008/0131049 A1 | 6/2008 | Koch et al. |
| 2009/0310140 A1 | 12/2009 | Smith et al. |
| 2009/0310902 A1 | 12/2009 | Smith et al. |

FOREIGN PATENT DOCUMENTS

| | | |
|---|---|---|
| WO | WO 01/40757 | 6/2001 |
| WO | WO 2005/116615 | 12/2005 |

OTHER PUBLICATIONS

Fan et al., "Coupling semiconductor nanocrystals to a fused-silica microsphere: a quantum-dot microcavity with extremely high Q factors," *Optics Letters*, vol. 25, No. 21 pp. 1600-1602 (Nov. 1, 2000).

Fano, "Effects of Configuration Interaction on Intensities and Phase Shifts," *Physical Review*, vol. 124, No. 6, pp. 1866-1878 (Dec. 15, 1961).

Götzinger et al., "Towards controlled coupling between a high-Q whispering-gallery mode and a single nanoparticle," *Appl. Phys. B*, vol. 73, pp. 825-828 (2001).

Little et al., "Second-order filtering and sensing with partially coupled traveling waves in a single resonator", *Optics Letters*, vol. 23, No. 20, pp. 1570-1572 (Oct. 15, 1998).

Soller et al., "Dynamic modifications to the plasmon resonance of a metallic nanoparticle coupled to a planar waveguide: beyond the point-dipole limit," *J. Opt. Soc. Am. B.*, vol. 19, No. 5, pp. 1195-1203 (May 2002).

Xu, et al., "Scattering-theory analysis of waveguide-resonator coupling," *Physical Review E*, vol. 62, No. 5, pp. 7389-7404 (Nov. 2000).

OPTICAL SENSING DEVICE

REFERENCE TO CO-PENDING APPLICATIONS

This application is related to a commonly-assigned patent application titled OPTICAL SENSING METHODS, having application Ser. No. 11/565,955, also filed on Dec. 1, 2006, which is incorporated herein by reference in its entirety.

FIELD OF THE INVENTION

The invention is directed generally to optical devices, and more particularly to optical sensors that use microresonators.

BACKGROUND

Optical sensing is becoming an important technology for detection of biological, chemical, and gaseous species. Optical sensing may offer advantages of speed and sensitivity. In recent years, many novel photonic structures and materials have been developed to make very sensitive optical devices.

One optical sensing method for analyte detection uses integrated optical waveguides. Such sensors have been demonstrated to be able to detect chemical and biological species adsorbed onto the waveguide surface. But integrated optical waveguide chemical analysis can require a large sensing device (typically several centimeters long) in order to obtain sufficient optical signal change for many analytical applications.

Surface plasmon resonance (SPR) has also been used to make optical sensors. SPR technology has been commercialized and it has become an essential tool to characterize and quantify biomolecular interactions. But such measurement systems can be bulky.

Optical microresonators are currently under intensive investigation for applications in biochemical, chemical, and gas sensing. Optical microresonators are very small devices that can have high quality factors (Q-factor) where Q-factor commonly refers to the ratio of a resonant wavelength to a resonance linewidth. For example, microresonators made of glass spheres can be used to make very sensitive optical sensors since the light trapped in the microsphere resonator circulates many times producing a device with a high Q-factor ($>10^6$) which allows effective enhancement of the optical interaction between an analyte on the surface of the microsphere and the light circulating in the resonator. In an optical microresonator sensor a bus waveguide is used to excite guided optical modes located close to the surface of the microresonator. One example of resonant optical modes is a whispering gallery mode. An analyte is then located within the evanescent field of the modes of the microsphere. The change in refractive index of the sensor is detected by a shift in the resonant frequencies. The shifted spectra can be extracted from the microresonator using a second bus waveguide that is connected to a detector.

A variety of types of optical microresonators have been investigated for the purpose of making optical sensors, but microspheres, microrings, and microdisks have received the most attention. Microdisks or microrings based on semiconductor fabrication processes are relatively easy to fabricate in a large quantity and/or high density. Their positions with respect to waveguides can be adjusted using fabrication technologies such as dry/wet etching and layer deposition. The Q-factors of these resonators, however, are typically below $10^4$, due at least in part to the surface roughness and to material absorption.

In the conventional approach to sensing using microspheres, bonding of an analyte to the surface of the sphere results in a small change in the effective refractive index of the sphere. This results in a small shift of the wavelength position of the peaks in the resonance spectrum. These shifts are typically in the picometer range. In order to detect such small shifts expensive equipment for spectral analysis is required. Furthermore, the microresonator must be designed to give a very narrow linewidth so that the small peak shifts can be detected. This requires a high finesse (free spectral range divided by linewidth), or equivalently, high quality factor (operating wavelength divided by linewidth) microresonator. This translates to the need for low loss waveguides in the microresonator and weak coupling between the microresonator and the bus waveguide in order to detect the small frequency shift.

There is a need for improved optical sensing systems that use microresonators.

SUMMARY OF THE INVENTION

Generally, the present invention relates to optical systems. The present invention also relates to optical sensors that include one or more microresonators.

In one embodiment, an optical sensing system includes a first and second bus waveguide. The first bus waveguide includes an input port that is in optical communication with a light source. The second bus waveguide includes a drop two port. The system further includes a microresonator optically coupled to the first and second bus waveguides and an optical scattering center configured for alteration of a strength of optical coupling between the optical scattering center and the microresonator. In addition, the system includes a detector in optical communication with the drop two port. The optical sensing system is configured so that, in the absence of a scattering center optically coupled to the microresonator, light launched at the input port couples to a first guided optical mode of the microresonator and the first guided optical mode primarily does not couple to the drop two port.

In another embodiment, an optical sensing system includes one or more bus waveguides, such as a first bus waveguide. The first bus waveguide includes an input port that is in optical communication with a light source. The system further includes a microresonator optically coupled to the one or more bus waveguides and a detector in optical communication with the input port.

In another embodiment, an optical sensing system includes a first bus waveguide, where the first bus waveguide includes an input port that is in optical communication with a light source. The system further includes a second bus waveguide having a drop port and a drop two port, a microresonator optically coupled to the first and second bus waveguides, and a detector in optical communication with the second bus waveguide. In the system, light launched at the input port is capable of coupling to a first guided optical mode of the microresonator and a second guided optical mode of the microresonator. The second optical mode occurs primarily when a scattering center is in optical communication with the microresonator. The drop port is primarily capable of optically coupling to the first guided optical mode of the microresonator and is primarily not capable of coupling to the second guided optical mode. The drop two port is primarily capable of optically coupling to the second guided optical mode of the microresonator and is primarily not capable of coupling to the first guided optical mode. The detector is in optical communication with the drop two port.

In yet another embodiment, an optical sensing system includes one or more bus waveguides, such as a first bus waveguide, where the first bus waveguide includes an input port that is in optical communication with a light source. The system further includes a disk microresonator optically coupled to the one or more bus waveguides, the disk microresonator defining a center location. The system also includes a detector in optical communication with the disk microresonator and located at the center location of the disk microresonator.

The above summary of the present invention is not intended to describe each illustrated embodiment or every implementation of the present invention. The figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
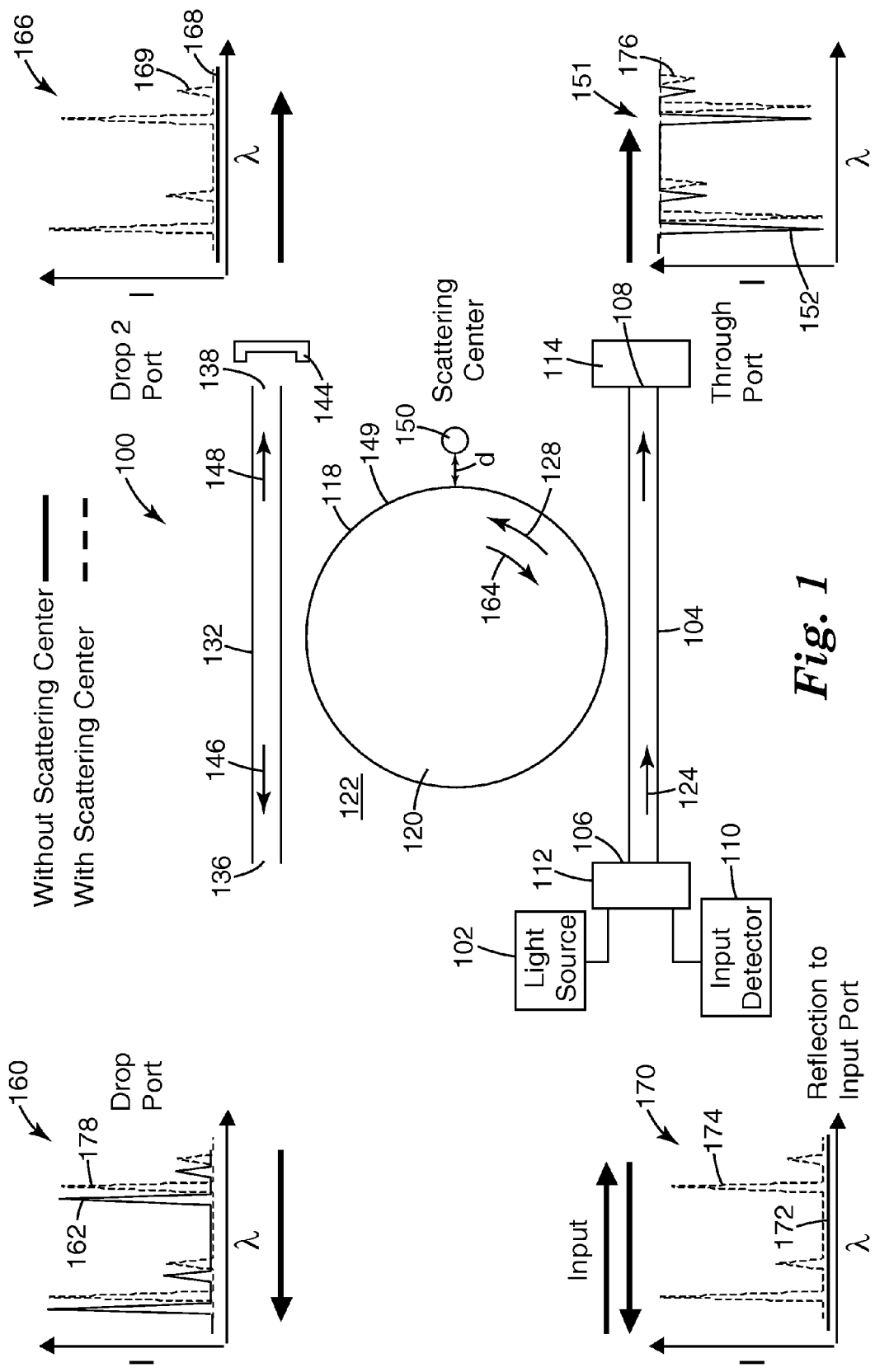
FIGS. 1, 2 and 3 are respective schematic top- and side-views of an optical system.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention describes an optical sensor that includes a waveguide, an optically resonant microcavity, and an optical scattering center that is optically coupled to the microcavity where the extent of the optical coupling can be changed. Such optically resonant microcavities may also be referred to as microresonators.

A new approach to optical sensing using microresonators is hereby presented in which the introduction or removal of the scattering center causes significant signal enhancement in a microresonator system. The significant signal enhancement enables the use of less expensive light sources and detectors than in previous microresonator sensing systems.

The present invention allows the use of broadband light sources and detectors in sensing applications and devices without sacrificing detection sensitivity. An advantage of using broadband sources and detectors is reduced overall device cost.

In the specification, a same reference numeral used in multiple figures refers to the same or similar elements having the same or similar properties and functionalities.

An example of a microresonator-waveguide system 100 that uses a microresonator will now be described, as schematically illustrated in top view FIG. 1 and cross-sectional views FIGS. 2 and 3. As will be further discussed herein, systems with a single waveguide may also be used according to the invention. However, a double bus waveguide system will be discussed as the first example.

Optical device 100 includes an optical microresonator 118, a first optical waveguide 104, and a second optical waveguide 132 all disposed on a lower cladding layer 105 disposed on substrate 103.

In some cases, microresonator 118 is capable of quantizing the allowed optical modes of the microresonator into discrete modes by imposing one or more boundary conditions, such as one or more periodicity conditions. In some cases, microresonator 118 is capable of supporting at least two different guided optical modes such as first guided optical mode 128 and second guided optical mode 164, where guided optical mode 128 is different than guided optical mode 164. In some cases, modes 128 and 164 have the same wavelength. In some cases, modes 128 and 164 have different wavelengths. If the modes 128 and 164 have substantially the same wavelengths, they may have different intensity levels for the wavelengths. As used herein, for a given optical configuration such as optical device 100, an optical mode refers to an allowed electromagnetic field in the optical configuration; radiation or radiation mode refers to an optical mode that is unconfined in the optical configuration; a guided mode refers to an optical mode that is confined in the optical configuration in at least one dimension due to the presence of a high index region; and a resonant mode refers to a guided mode that is subject to an additional boundary condition requirement in the optical configuration, where the additional requirement is typically periodic in nature.

Resonant modes are typically discrete guided modes. In some cases, a resonant mode can be capable of coupling to a radiation mode. In some other cases, a resonant mode can have a component that is radiation and not confined. In general, a guided mode of microresonator 118 can be a resonant or a non-resonant mode. For example, optical modes 128 and 164 can be resonant modes of microresonator 118.

In some cases, first guided optical mode 128 and/or second guided optical mode 164 is capable of propagating within the microresonator while maintaining a same electric field profile. In such cases, the shape or profile of the propagating mode remains substantially the same over time even if the mode gradually loses energy because of, for example, absorption or radiation losses.

Figure 2:
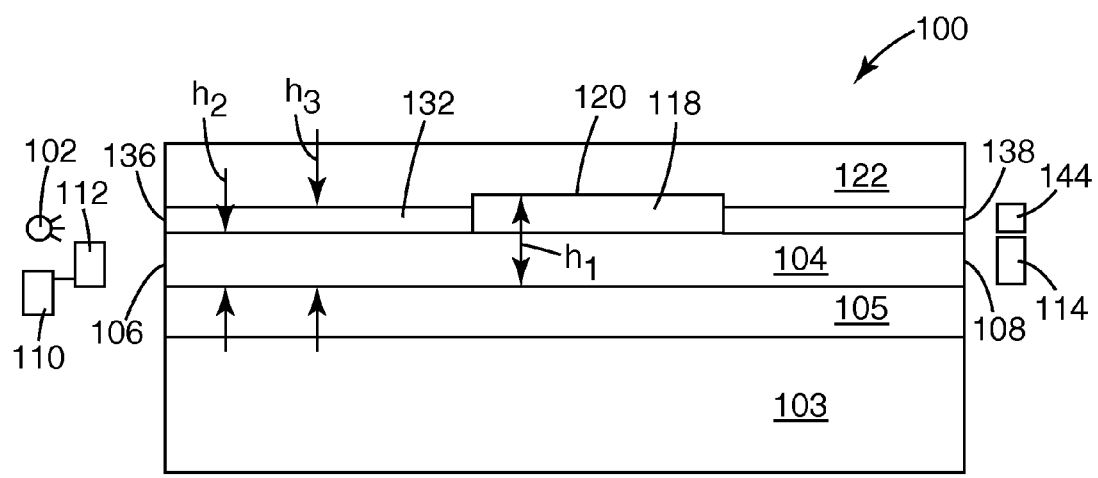
Figure 3:
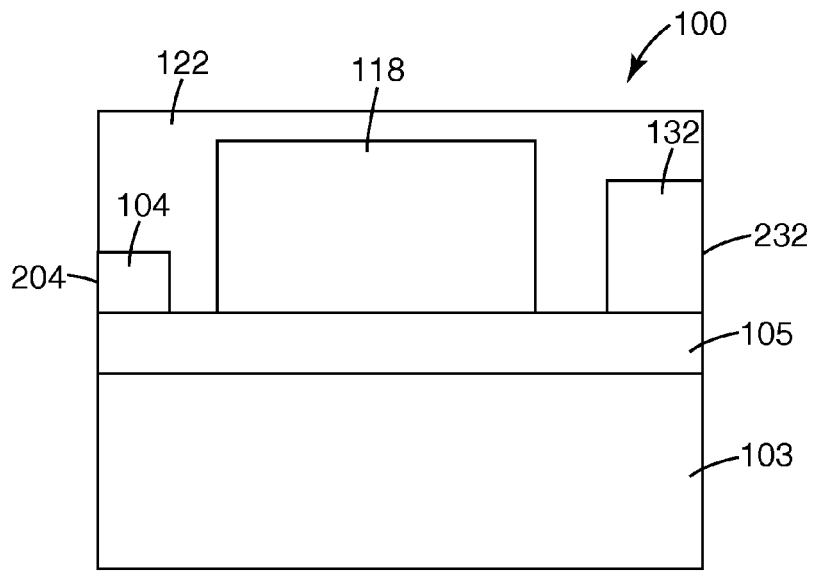

Referring to FIGS. 1-3, a light source 102 is in optical communication with the first bus waveguide 104. The end of the waveguide 104 where the light source is located is an input port 106. Another end of the waveguide 104 is the through port 108. An input port detector 110 is located at the input port 106. An optical component 112 is in optical communication with the light source 102, input detector 110, and input port 106 to allow input light 124 to communicate only with the input port 106, and allow light traveling toward the input port 106 in the first bus waveguide 104 to be directed toward the input detector 110. The optical component 112 is an optical splitter or optical circulator in certain embodiments. The input port detector 110 is in optical communication with the first bus waveguide 104, via the optical component 112, and is configured to detect light.

The microresonator 118 is capable of supporting first and second resonant optical modes 128 and 164, respectively, and is optically coupled to the first bus waveguide 104. Input port 106 is capable of optically coupling to both first and second resonant modes. Light 124 from the light source 102 is launched into the first bus waveguide 104 and propagates towards the through port 108. The microresonator 118 evanescently couples some of the light 124 out of the first bus waveguide 104, the out-coupled light propagates within the microresonator 118 at one or more of the resonant frequencies of the microresonator 118, such as first resonant optical mode 128. Microresonator 118 includes a core 120 and a cladding 122. In some embodiments, the upper cladding 122 can include water. In some cases, the upper cladding can include different materials, for example, at different locations. For example, some regions of the upper cladding can include water and some other regions of the upper cladding can include another material such as glass.

A second bus waveguide 132 is positioned in optical communication with the microresonator 118. A drop port 136 is located at one end of the second bus waveguide 132, while a drop 2 port 138 is located at another end of the second bus waveguide. The drop port 136 is primarily capable of optically coupling to the first but not the second resonant optical mode. The drop 2 port 138 is primarily capable of optically coupling to the second but not the first resonant guided optical mode. A drop 2 port detector 144 is located at the drop 2 port 138.

The microresonator 118 may be positioned in physical contact with, or very close to, the waveguides 104 and 132 so that a portion of the light propagating along the waveguides is evanescently coupled into the microresonator 118. Also, a portion of light propagating within the microresonator 118 will be evanescently coupled into the waveguides 104 and 132.

FIG. 2 is a view of a cross-section through the first bus waveguide 104 and along an axis of the first bus waveguide. FIG. 3 is a view of a cross-section through the microresonator 118 and the two bus waveguides and perpendicular to an axis of the first bus waveguide. Each of the first and second optical waveguides has a core disposed between multiple claddings. For example, first optical waveguide 104 has a core having a thickness $h_2$ and disposed between upper cladding 122 and lower cladding 105. Similarly, second optical waveguide 132 has a core having a thickness $h_3$ disposed between upper cladding 122 and lower cladding 105. In some cases, upper cladding 122 can include air or water.

In the exemplary optical device 100 of FIGS. 1-3, microresonator 118 and optical waveguides 104 and 132 have different thicknesses. In general, thicknesses $h_1$, $h_2$, and $h_3$ may or may not have the same value. In some applications, microresonator 118 and optical waveguides 104 and 132 have the same thickness.

The impact of a scattering center upon the microresonator system 100 is central to the method of the invention. FIG. 1 illustrates a scattering center 150 in optical communication with the microresonator 118. However, before the effect of the scattering center 150 is described, the use of a microresonator system 100 without a scattering center 150 will be described.

In one conventional approach to sensing using microresonators, a surface 149 of a core 120 of the microresonator 118 is functionalized to be capable of chemically specific bonding with an analyte. Bonding of an analyte to the surface of the microresonator causes a small change in the effective refractive index of the microresonator, which shifts the wavelength position of the peaks in the resonator transmission spectrum. These shifts are observed at the through port 108 and the drop port 136. Hence, the detection of a shift of the peaks of the transmission spectrum at the through port 108 and/or drop port 136 indicates the presence of an analyte. Other conventional approaches to sensing using microresonators exist, and some examples of various approaches are detailed in commonly-owned U.S. Published Patent Application 2006/0062508 which is incorporated herein by reference.

Light 124 emitted by the light source 102 travels through the first bus waveguide 104 and the microresonator 118 evanescently couples some of the light 124 out of the first bus waveguide 104, so that the out-coupled light propagates within the microresonator 118 at one or more of the resonant frequencies of the microresonator 118, such as first optical resonant mode 128. One example of resonant modes of a microresonator is "whispering gallery modes". In geometric optics, light rays in a whispering gallery mode (WGM) propagate around the microresonator from an origin via a number of total internal reflections, until they return to the origin. In addition to WGMs, many other resonant modes are possible for microresonators.

For a high-quality microresonator in the absence of a scattering center, the first resonant mode 128 couples to the through port 108 and the drop port 136, where a detector can detect the spectrum of the resonant frequencies in the microresonator. The resonant mode 128 couples weakly or essentially does not couple to the drop 2 port 138 or the input port 106. Through port output graph 151 illustrates an example of the light spectrum that is detected at the through port 108, graphing intensity against wavelength. The solid line 152 is an example of a light spectrum that may be detected in the absence of a scattering center. The intensity minima of plot 152 will experience a shift on the order of a few picometers when, for example, the effective refractive index of the microresonator 118 is modified, for example increased, due to, for example, bonding of an analyte to the surface of the waveguide. In this way, bonding of an analyte to the surface 149 of the microresonator is detected in one example of conventional sensing systems.

Similarly, light 128 propagating within the microresonator 118 couples to the second bus waveguide 132 and is detected at the drop port 136. Drop port output graph 160 illustrates an example of the light spectrum that is detected at the drop port 136, graphing intensity against wavelength. The solid line 162 is an example of a light spectrum that may be detected without a scattering center. The peaks of plot 162 will experience a shift on the order of a few picometers when the effective refractive index of the microresonator 118 is modified due to bonding of an analyte to the surface 149 of the waveguide.

In order to detect a spectrum shift on the order of a few picometers at the drop port 136 or through port 108, a fairly expensive tunable narrow-linewidth laser source is used to scan the relevant spectral region of the resonator output spectrum. Alternatively, a broadband source and an expensive spectrum analyzer can be used. In addition, the microresonator 118 is designed to yield a narrow linewidth, so that the small peak shifts can be detected. The microresonator can yield a narrow linewidth by using a high finesse, which is the free spectral range divided by linewidth. The microresonator can also yield a narrow linewidth by using an equivalently high quality factor, which is the operating wavelength divided by linewidth. This can be achieved by, for example, using a low loss resonator that is weakly coupled to the bus waveguides.

Compared to the exemplary sensing approach described above, the use of a scattering center sensing approach of the present invention leads to much larger changes in the spectral positions of resonance peaks at the drop port 136 and through port 108, typically on the order of nanometers instead of picometers. In addition, large changes in the broadband transfer characteristics of the resonator are observed. These transfer characteristics can be observed at the drop 2 port and input port and have the potential to simplify the system by eliminating the need for a narrow-linewidth tunable laser source.

During a sensing event according to one embodiment of the present invention, the strength of optical coupling between a scattering center and a microresonator is altered. This occurs by, for example, a scattering center becoming optically coupled to the microresonator, or by a scattering center being removed from optical coupling with the microresonator. When the scattering center is optically coupled to the microresonator, the optical fields of one or more of the resonator's modes overlap with the scattering center.

Again referring to FIG. 1, when a scattering center 150 is in optical communication with the microresonator, the first resonant optical mode 128 is scattered to at least a second guided optical mode 164, different from a first resonant optical mode. The second guided optical mode couples primarily to the input port 106 and drop 2 port 138. Graph 166 illustrates the spectrum of the light output at the drop 2 port 138. The solid line 168 is the plot of light output when no scattering center is present. Essentially no light is distributed to the drop 2 port when no scattering center is present. The dashed line 169 illustrates the spectrum of light output at the drop 2 port 138 when a scattering center 150 is in optical communication with the microresonator. Significant peaks are observed in plot 169. The presence of a scattering center therefore leads to a large transfer of energy to the drop 2 port for a broad range of operating frequencies. As a result, it will be straightforward to detect whether a scattering center is attached to the microresonator by monitoring the output at the drop 2 port 138. The output can be monitored for larger peaks at specific wavelengths and/or for greater light output across all wavelengths.

A similar change is observed at the input port 106. Graph 170 illustrates the spectrum of light output from the input port 106, as detected by the input port detector 110, at a conceptual level. Solid line plot 172 illustrates the light output when no scattering center is present, which is close to zero. Dashed line plot 174 illustrates the spectrum of light output when a scattering center is attached to the microresonator. Significant peaks are observed in plot 174 compared to plot 172. The presence of a scattering center therefore leads to a large transfer of energy reflected back to the input port 106 for a broad range of operating frequencies. As a result, it will be straightforward to detect whether a scattering center is attached to the microresonator by monitoring the output of at the input port 106. The output can be monitored for larger peaks at specific wavelengths and/or for greater light output across all wavelengths.

The optical scattering from the first mode to the second mode due to a scattering center can be observed at the input port, the drop 2 port or both locations. Accordingly, various embodiments include detectors at only the input port, only the drop 2 port, or both the input and drop 2 ports.

The presence of a scattering center optically coupled to the microresonator also causes a change in the output observed at the through port 108 and the drop port 136. In one particular embodiment of the invention, a scattering center with a refractive index that is different than the cladding materials of the environment, which is water for most bio-sensing system, induces a large resonance line frequency shift on the scale of nanometers. In some cases, there is a large difference between the cladding index and the scattering center index where each index can be a complex index of refraction. The frequency shift is conceptually illustrated in FIG. 1. At the through port 108, the solid line 152 of graph 151 illustrates the spectrum that is detected at through port detector 114 without a scattering center present. Dashed line 176 illustrates the spectrum that is detected when a scattering center is brought into optical coupling with the microresonator, where the peaks are shifted compared to plot 152. In the exemplary graph 152, the shift is toward longer wavelengths or a red shift corresponding to, for example, the real part of the refractive index of the scattering center being greater than the index of the cladding materials.

A similar change is seen at the drop port 136, where dashed line 178 illustrates the spectrum with a scattering center, and solid line 162 illustrates the spectrum without a scattering center. A microresonator sensing system using a scattering center and a frequency shift at the output at the drop port or through port to detect an alteration in the strength of coupling of a scattering center is described in detail in co-owned and co-pending patent application Ser. No. 11/565,935, titled "Optical Microresonator", filed on the same date as the present application. Accordingly, in various sensing systems, detectors are located at the drop port 136, the through port 108, or both.

Figure 4:
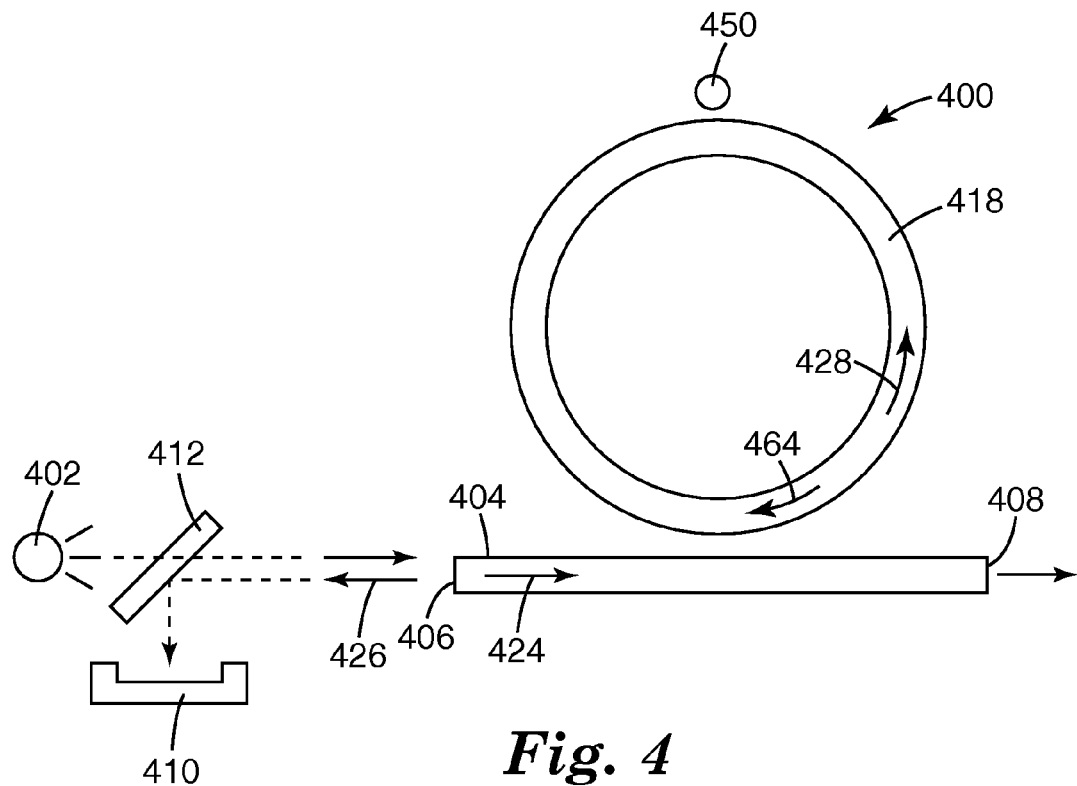
FIG. 4 is a schematic top-view of an optical system with a single-bus ring resonator.

FIG. 4 is a schematic illustration of a single bus ring resonator embodiment 400, where a light source 402 is in optical communication with the single waveguide 404 at an input port 406. An input port detector 410 is positioned at the input port 406. An optical component 412, such as an optical splitter or optical circulator, is in optical communication with the input port 406, the light source 402, and the input port detector 410.

A ring microresonator 418 is in optical communication with the waveguide 404. Light 424 from the light source 402 is launched into the first bus waveguide 404 and propagates towards the through port 408. The microresonator 418 evanescently couples some of the light 424 out of the first bus waveguide 404, the out-coupled light propagates within the microresonator 418 at one or more of the resonant frequencies of the microresonator 418, such as first resonant optical mode 428.

During a sensing event according to one embodiment of the present invention, the strength of optical coupling between a scattering center 450 and a microresonator 418 is altered. When a scattering center 450 is in optical communication with the microresonator, the first guided optical mode 428 is scattered to at least a second guided optical mode 464, different from a first guided optical mode. The second guided optical mode couples primarily to the input port 406 and exits the input port as light 426. The presence of a scattering center leads to a large transfer of energy reflected back to the input port 406 for a broad range of operating frequencies. As a result, the change of coupling of the scattering center can be ascertained by monitoring light 426 at the input port 406 via detector 410.

In an alternate embodiment, the ring resonator 418 is replaced with a disk resonator.

Figure 5:
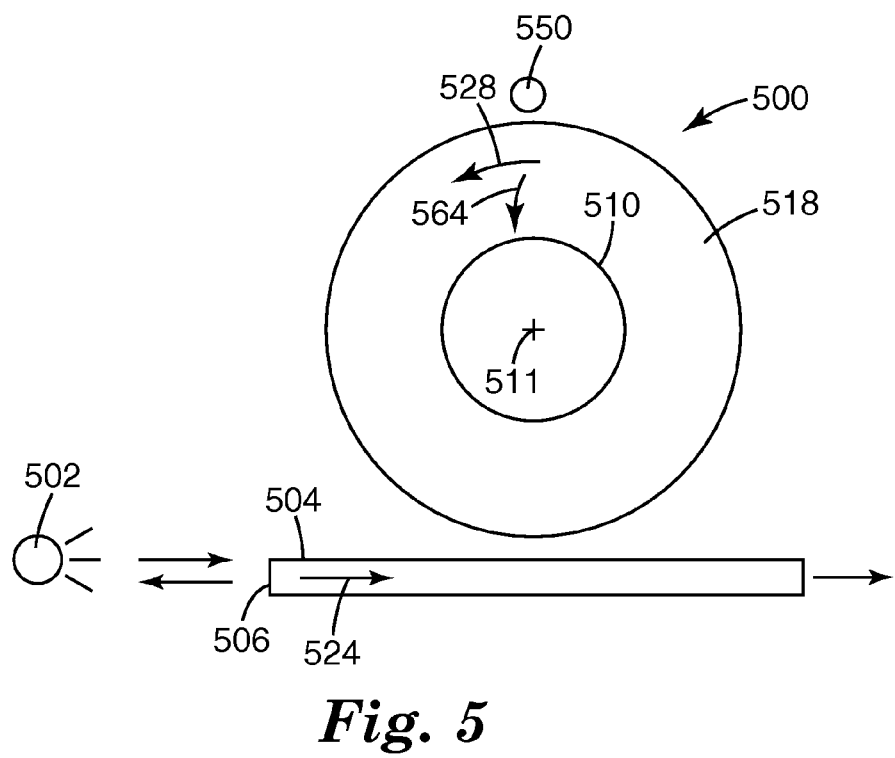
FIG. 5 is a schematic top-view of an optical system with a single-bus disk resonator with a center photodetector.

FIG. 5 is a schematic illustration of a single bus disk resonator embodiment 500, including a light source 502 in optical communication with the single waveguide 504 at an input port 506, to provide light 524 to the waveguide 504. Unlike other embodiments illustrated herein, a light detector 510 is positioned at a center 511 of a disk resonator 518 instead of at a waveguide port. A scattering center 550 is brought into or removed from optical communication with microresonator 518. For the illustrated embodiment, the step of detecting induced scattering between the first resonant optical mode 528 and a second guided optical mode 564 includes detecting the induced scattering at a center location of the microresonator 518.

Figure 6:
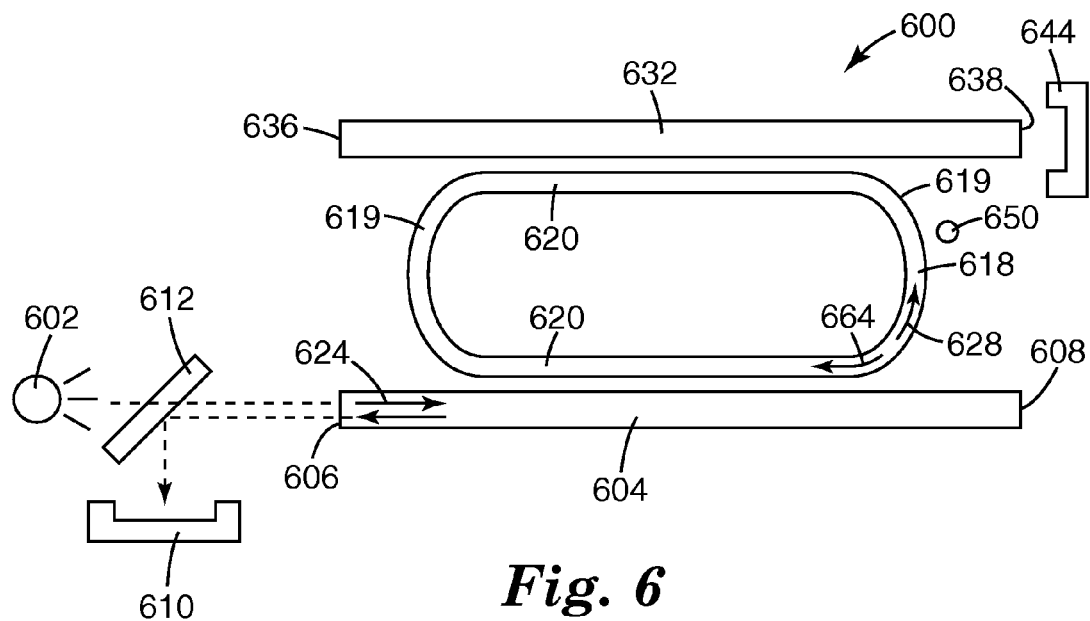
FIG. 6 is a schematic top-view of an optical system with a double-bus racetrack ring resonator.

FIG. 6 is a schematic view of a double bus waveguide racetrack microresonator embodiment 600, where a light source 602 is in optical communication with a first waveguide 604 at an input port 606. An input port detector 610 is positioned at the input port 606. A through port 608 is present at the other end of the first waveguide 604. An optical component 612, such as an optical splitter or optical circulator, is in optical communication with the input port 606, the light source 602, and the input port detector 610.

Light 624 from the light source 602 is launched into the first bus waveguide 604 and propagates towards the through port 608. A racetrack microresonator 618 includes two curved portions 619 and two linear portions 620. The microresonator 618 evanescently couples some of the light 624 out of the first bus waveguide 604, the out-coupled light propagates within the microresonator 618 at one or more of the resonant frequencies of the microresonator 618, such as first resonant optical mode 628. In some cases, the racetrack 618 is a single transverse mode racetrack, meaning that the racetrack supports a single mode in a direction transverse to the direction of light propagation within the racetrack. In some other cases, the racetrack 618 is a multi transverse mode racetrack.

A second bus waveguide 632 is positioned in optical communication with the microresonator 618. A drop port 636 is located at one end of the second bus waveguide 632, while a drop 2 port 638 is located at another end of the second bus waveguide 632. The drop port 636 is primarily capable of optically coupling to the first guided optical mode 628. The drop 2 port 638 is capable of very weak coupling or is not capable of coupling to the first guided optical mode. A drop 2 port detector 644 is located at the drop 2 port 638.

The optical scattering from the first mode to the second mode due to a scattering center 650 can be observed at the input port 606, the drop 2 port 638 or both locations. Accordingly, various embodiments include a detector in optical communication with the input port 606, a detector in optical communication with the drop 2 port 638, or first and second detectors in optical communication with the input and drop 2 ports, respectively.

Additional embodiments of microresonator waveguide systems that are configured to induce optical scattering from a first resonant guided optical mode to at least a second guided optical mode are illustrated and described in commonly-owned U.S. patent application Ser. No. 11/565,935, titled "Optical Microresonator", filed on the same date as the present application, the entirety of which is incorporated herein by reference.

A scattering center is an element that, when optically coupled to a microresonator, is able to perturb the wave function of the resonant modes within the microresonator to cause a transfer of energy from modes that are excited by input in the absence of the scattering center (such as at least first resonant optical mode 128 in FIG. 1) to modes that are not excited in the absence of the scattering center (such as at least second guided optical mode 164 in FIG. 1). In an embodiment, the scattering center increases the transfer of energy from a first mode to a second mode, though some transfer of energy from the first mode to second mode may occur even in the absence of the scattering center.

Examples of scattering centers that may be used with the present invention sensing methods include nanoparticles. As used herein, the term "nanoparticles" refers to particles having a maximum dimension on the order of 1000 nanometers or less. In certain embodiments, the scattering center is at least 20 nanometers, at most 100 nanometers, or both. In other embodiments, the scattering center is at least 10 nanometers, at most 150 nanometers, or both.

In one embodiment of the invention, the scattering center has a high index difference compared to the medium that will surround the scattering center during a sensing event, which is typically water. In an embodiment of the invention, the scattering center has a high absorption value. For example, the imaginary part of the complex refractive index of the scattering center material is at least 8.

In some cases, such as in the case of some metals such as gold, the real part of the index of refraction of the scattering center is less than 1. In some other cases, such as in the case of silicon, the real part of the index of refraction of the scattering center is greater than 2.5.

Examples of scattering centers that are appropriate for use with the invention include silicon nanoparticles and metal nanoparticles, including gold and aluminum nanoparticles. In some cases, a scattering center may be a semiconductor such as Si, GaAs, InP, CdSe, or CdS. For example, a scattering center can be a silicon particle having a diameter of 80 nanometers and an index of refraction (the real part) of 3.5 for a wavelength of interest. Another example of a scattering center is a gold particle having a diameter of 80 nanometers and an index of refraction of 0.54+9.58 i for wavelengths near 1550 nm. Another example of a scattering center is an aluminum particle having a diameter of 80 nanometers and an index of refraction of 1.44+16.0 i for wavelengths near 1550 nm.

In some embodiments, the scattering center is a dielectric particle. The scattering center is a non-fluorescent particle in many embodiments. Further, the scattering center is not a semiconductor in some embodiments.

Now referring to the example of FIG. 1 to illustrate an issue that relates to all the examples, a change in the strength of optical coupling between scattering center 150 and microresonator 118 can induce a change in optical scattering between first and second guided optical modes 128 and 164, respectively. The change in the strength of optical coupling can be achieved by various means. For example, a change in the spacing "d" between scattering center 150 and microresonator 118 can change the strength of optical coupling between the scattering center and the microresonator. In another example, a change in the index of refraction, $n_s$, of the scattering center can change the strength of optical coupling between the scattering center and the microresonator. In one embodiment, the scattering center is a region of variable refractive index embedded in the core of the resonator. In such a case, the index of refraction can change when, for example, the region is exposed to and absorbs a material such as gas or liquid. In general, any mechanism that can cause a change in the strength of optical coupling between scattering center 150 and microresonator 118 can induce a change in optical scattering between modes 128 and 164.

There are several approaches to using the microresonator waveguide system as a sensor. The choice of approach is determined by a variety of considerations, including the chemistry of the analyte to be detected, the time available for detection, the sample preparation technology, etc. One example of using a scattering center in a detector system involves coating the resonator with an antibody for a specific antigen. An antibody is a protein used by the immune system to identify and neutralize foreign objects like bacteria and viruses. Each antibody recognizes a specific antigen as its unique target.

In one approach, the sample to be analyzed is prepared such that scattering center labels, such as nanoparticle labels, are selectively attached to the antigen molecules, by functionalizing the nanoparticles with a corresponding antibody before mixing them with the sample. The sample is then brought into contact with the surface of the microresonator. When the binding between the antibody-functionalized resonator and the nanoparticle-labeled antigen occurs at the surface of the resonator, the nanoparticle is brought into optical coupling range, and a signal would be detected at the drop two or input ports where there previously was not a significant signal. The same or a similar approach is used to detect bacteria, viruses and spores, as well as protein and DNA.

Sensing by removal of a scattering center from the resonator is accomplished by first binding the scattering center to the resonator with an antigen-antibody system having weaker binding than the antigen-antibody reaction resulting when the analyte is introduced. Competition for binding to the resonator would result in separation of the scattering center from the vicinity of the resonator, and loss of optical coupling with the scattering center. A similar approach allows detection of any chemical species capable of selectively severing chemical bonds between the nanoparticle and resonator.

The light source 102 generates light 124 at a desired wavelength, or wavelength range. For example, where the microresonator is used in a sensor, the light source 102 generates light at a wavelength that interacts with the scattering center that is being introduced to or removed from optical communication with the microresonator. In existing sensing systems using microresonators, it is particularly important that the light source produces light that is efficiently coupled into the first bus waveguide 104. This leads to the frequent use of light sources such as lasers, such as a laser diode. Lasers, such as laser diodes, are appropriate light sources for use with embodiments of this invention. In addition, the approach of the present invention allows the use of a light source that generates a broader range of wavelengths than light sources in existing sensing systems. In an embodiment, the light source 102 includes a lamp, along with suitable optics for coupling light from the lamp into the first bus waveguide 104. In some applications, light source 102 can be a light emitting diode (LED) or a laser such as a laser diode. In an embodiment, the lamp is a broadband light source, emitting a number of or a range of frequencies rather than one specific wavelength or narrow range of wavelengths. In some applications, the light source can be a broadband light source emitting, for example, white light. In some cases, light source 102 can emit light having at least one wavelength in a range from about 400 nm to about 2000 nm. In some other cases, the range can be from about 700 nm to about 1600 nm. In some other cases, the range can be from about 900 nm to about 1400 nm. In some cases, light source 102 can emit light at 633 nm, 850 nm, 980 nm, 1310 nm, or 1550 nm.

The first bus waveguide 104 may be any suitable type of waveguide and may be, for example, a channel waveguide formed in or on a substrate, such as a waveguide formed in or on a silicon substrate. The first bus waveguide 104 may also be an optical fiber.

The detector unit 110 includes a light detector, for example a photodiode or phototransistor, to detect light. The detector unit 110 may also include a wavelength sensitive device that selects the wavelength of light reaching the light detector. The wavelength selective device may be, for example, a filter, or a spectrometer. The wavelength selective device may be tunable so as to permit the user to actively change the wavelength of light incident on the light detector. In some cases, a wavelength selective device may be employed at other ports such as the drop two port.

Microresonator 118 of FIG. 1 is shown to be a disk microresonator. In general, microresonator 118 can be any type resonator, such as any shape microcavity, capable of supporting multiple guided optical modes and capable of coupling to one or more optical waveguides. For example, microresonator 118 can be a ring microresonator, closed loop microresonator, a sphere microresonator, a toroidal microresonator, a disk microresonator, or a racetrack microresonator. In the various exemplary embodiments discussed herein, any of these microresonator types could be substituted for another to create alternate embodiments. Since the fabrication process for ring and disk microresonators is compatible with standard microelectronic processes, these devices offer considerable potential for low cost manufacturing and robust systems.

In some cases, the microresonator has circular symmetry, meaning that the perimeter of a cross-section of the core of the microresonator can be expressed as a function of distance from a central point only. In some cases, such as in a disk-shaped microresonator, the center point can be the center of the microresonator. Exemplary microresonator shapes having circular symmetry include a sphere, a toroid, a disk, and a cylinder. In some cases, the microresonator can have spherical symmetry such a sphere-shaped microresonator.

The microresonator 118 typically has a diameter in the range from 2 μm to a few millimeters, but is more often in the range 5 μm-500 μm. In some cases, the range is from about 5 μm to about 100 μm.

In some cases, the bus waveguides and the microresonators as well as the light sources and the detectors of this invention are integrated onto a common substrate. The integration may be a monolithic integration, in which case the different components are all fabricated onto the common substrate typically using the same material systems. Such an integration can be substrate specific, meaning that the integration may be easier or feasible for some substrates and harder or not possible for some other substrates. For example, it may be possible to fabricate or grow the detector, the microresonator, and the waveguides on a substrate, such as a Si substrate, but it may be difficult or not possible to grow or fabricate the light source on the same substrate. As another example, it may be possible to grow or fabricate all the system components on a III-V semiconductor substrate such as an InP or GaAs substrate.

The integration can be a hybrid integration, in which case at least some of the components are first fabricated separately and then assembled onto a common substrate. The assembly can be done by, for example, adhesively bonding the detector and the light source onto the substrate. In such a case, the microresonator and the waveguides may be monolithically integrated onto the substrate. In some cases, the bonding may require active alignment of the light source and the detector with the bus waveguides.

In certain embodiments, the common substrate is a conventional substrate used for integrated optics such as silicon dioxide that has a refractive index that is substantially lower than the materials used to make the bus waveguides and microresonators (or light sources and photodetectors). It is contemplated that the substrates may include flat, solid materials such as glass or smooth, flexible materials such as polymeric substrates. Polyester, polyacrylate and polyimide substrates, for example, may be useful in this invention. The substrate may be optically opaque or transmissive. The substrate may be polymeric, a metal, a semiconductor, or any type of glass. In one example, the substrate is silicon. As another example, the substrate may be float glass or it may be made of organic materials such as polycarbonate, acrylic, polyethylene terephthalate (PET), polyvinyl chloride (PVC), polysulfone, and the like.

To make integrated devices, typically a high index material or high index materials are deposited onto a substrate and patterned so as to form the one or more bus waveguides and the microresonator. The patterning can be done by additive methods such as vapor deposition through a mask, printing, or a lift-off process. Thermal evaporation, sputtering, printing, molecular beam epitaxy (MBE), metal organic chemical vapor deposition (MOCVD), vapor phase epitaxy (VPE), and chemical vapor deposition are all examples of methods that can be used to deposit the waveguides, microresonators, or other optical components onto the substrate. It is also possible to pattern the waveguide elements onto the substrate by subtractive methods such as etching, such as reactive ion etching or wet chemical etching. In some applications, the resonator, the optical waveguides, the light source and the detector are integrated onto the same substrate. The integrated device or parts of the integrated device can be fabricated by, for example, a molding process.

Waveguides coupled to resonators are often tapered to increase the intensity of the optical field intensity outside the waveguide, thus increasing the amount of light that couples into the microresonator. In the case of an optical fiber waveguide, the fiber may be heated and tapered or etched to a total thickness of about 1-5 µm. Likewise, with a planar or channel waveguide, the waveguide thickness may be reduced at the region where the light is coupled to the microresonator. In addition to the waveguide being reduced in size, the thickness of the cladding around the waveguide may also be reduced. Various approaches to coupling the microresonator to a waveguide or fiber are discussed in greater detail in commonly owned and co-pending U.S. Patent Published Application No. 2005-0077513, incorporated herein by reference.

There are many different examples of how a waveguide can be coupled to a microresonator resulting in a microresonator structure with an acceptable amount of optical loss and an acceptable manufacturing process. For example, FIG. 3 illustrates lateral coupling of the first bus waveguide 104 and the second bus waveguide 132 to the microresonator 118. In this configuration, the optical coupling between the waveguides 104, 132 and the microresonator 118 occurs in a sideways or lateral direction as the structure is oriented in FIG. 3. In certain embodiments, cladding is present on the outside sides 204, 232 of the waveguides 104, 132 to push the waveguide modes towards the resonator for enhanced coupling as described in, for example, commonly-owned U.S. patent application Ser. No. 11/277,769 which is incorporated herein by reference. There are many other options for configuring the cladding on the waveguides 104, 132 to accomplish coupling between the waveguides 104, 132 and the microresonator 118.

In some embodiments of a lateral coupling configuration, the waveguides 104, 132 and the microresonator 118 are fabricated using the same patterning step.

Figure 13:
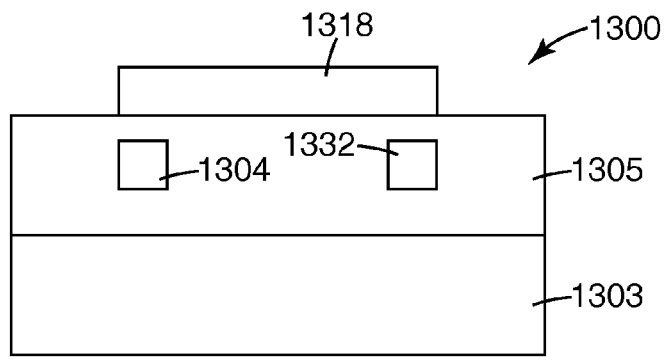
FIG. 13 is a schematic side view of an optical device with vertical coupling between two bus waveguides and a microresonator.

An alternative to the lateral coupling configuration of FIG. 3 is a vertical coupling configuration, an example of which is illustrated in FIG. 13. The vertically coupled optical device 1300 includes an optical microresonator 1318, a first optical waveguide 1304, and a second optical waveguide 1332 all embedded in a lower cladding layer 1305 disposed on a substrate 1303. The waveguides 1304, 1332 are surrounded by a cladding layer 1305. In a vertical coupling configuration, the optical coupling between the waveguides 1304, 1332 and the microresonator 1318 occurs in a vertical or up-and-down direction, as the optical device 1300 is oriented in FIG. 13.

In some embodiments of a vertical coupling configuration, the waveguides 1304, 1332 are patterned in a separate lithography step from the microresonator 1318.

In some cases, the coupling between a microresonator and a bus waveguide is an evanescent coupling, meaning that the cores of the microresonator and the bus waveguide are not in contact but are close enough to one another so that the evanescent tails of the microresonator and the waveguide overlap in a cladding region between the two cores.

In some other cases, the cores of the microresonator and the bus waveguide are in physical contact as detailed in the co-pending patent application Ser. No. 11/565,935, titled "Optical Microresonator", filed on the same date as the present application. In such cases, the coupling between the microresonator and the bus waveguide can be referred to as a core coupling.

Figure 14:
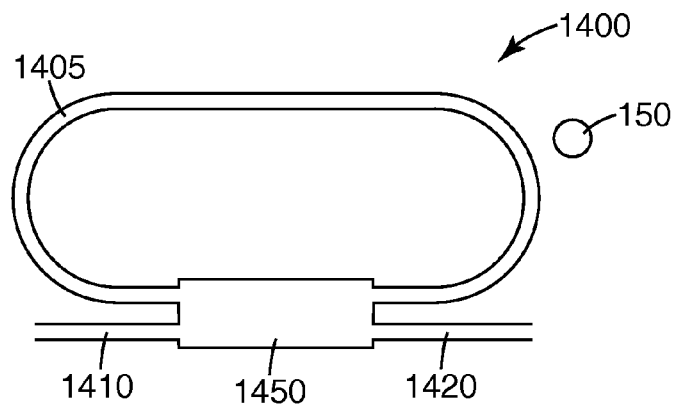
FIG. 14 is a schematic top-view of an optical system with a racetrack ring resonator coupled to two bus waveguides via a multimode interference coupler.

In some cases, the coupling between a microresonator and a bus waveguide can be carried out via a multimode interference coupler schematically illustrated in FIG. 14. Optical system 1400 includes a microresonator 1405 optically coupled to a first bus waveguide 1410 and a second bus waveguide 1420 via a multimode interference coupler (MMIC) 1450 where the MMIC can, for example, be rectangular. Optical interference within the MMIC determines what fraction of light launched in waveguide 1410 couples to microresonator 1405 and what fraction couples to second bus waveguide 1420. In the exemplary optical system 1400, waveguides 1410 and 1420 are collinear. In general, the two bus waveguides may or may not be collinear.

A microring resonator system with two bus waveguides was numerically analyzed using an effective two dimensional finite difference time domain (FDTD) simulation. Different simulations were performed to demonstrate the effect of various types of scattering centers optically coupled to the microring resonator system. The modeled system is similar to the system 100 illustrated in FIG. 1, but with a single mode microring resonator instead of a disk resonator 118. The ring diameter was 3.6 microns and the effective index of the core of the ring was 3. A water cladding having n=1.33 was assumed to be surrounding the ring resonator. Light was launched from a broadband source, having a wavelength of 1-3 microns.

Figure 7:
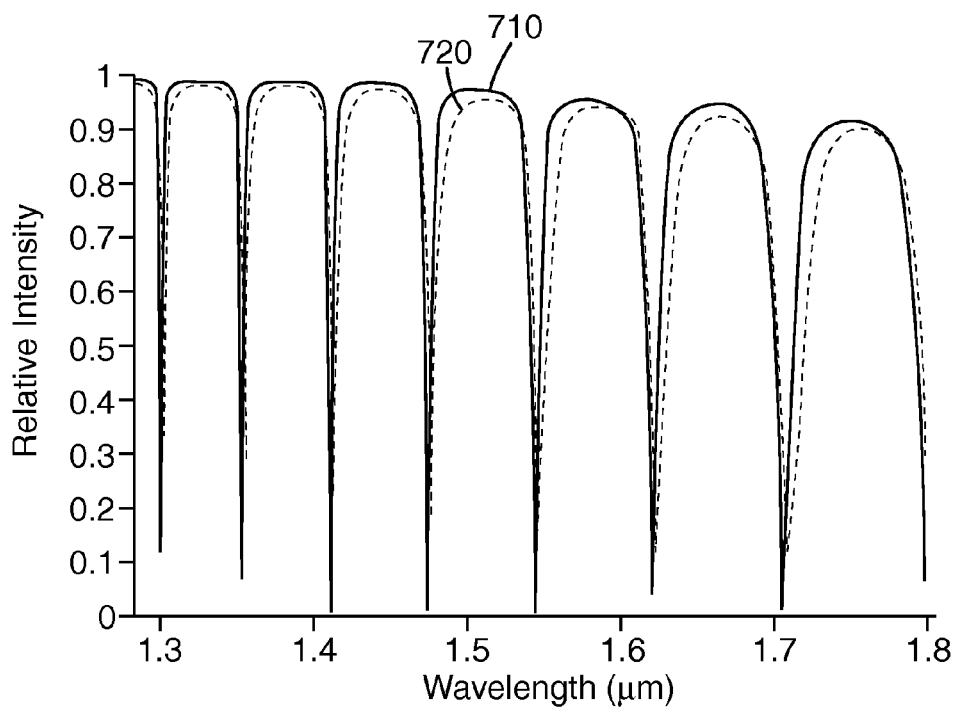
FIG. 7 is a plot of signal strength against wavelength, as detected at a through port of an optical system, with and without a silicon nanoparticle scattering center.

A first example demonstrates the effect of a silicon nanoparticle attached to a ring resonator with two bus waveguides, where the nanoparticle has a diameter of 80 nanometers and an index of refraction of 3.5. In FIG. 7, the signal strength is plotted on the y-axis, in arbitrary units relative to the intensity of the input light, against the wavelength on the x-axis. The signal is detected at the through port is illustrated in FIG. 7, where plot 710 represents the output for the ring with a water cladding only, and plot 720 represents the output for the ring optically coupled to the silicon nanoparticle. For the through port spectrum, a peak shift of about 2 nanometers occurs at a wavelength of 1.55 micron. At other resonance wavelengths, considerable shifts are observable on a nanometer scale, demonstrating the increased sensitivity of the technique of using nanoparticles in the sensing method.

Figure 8:
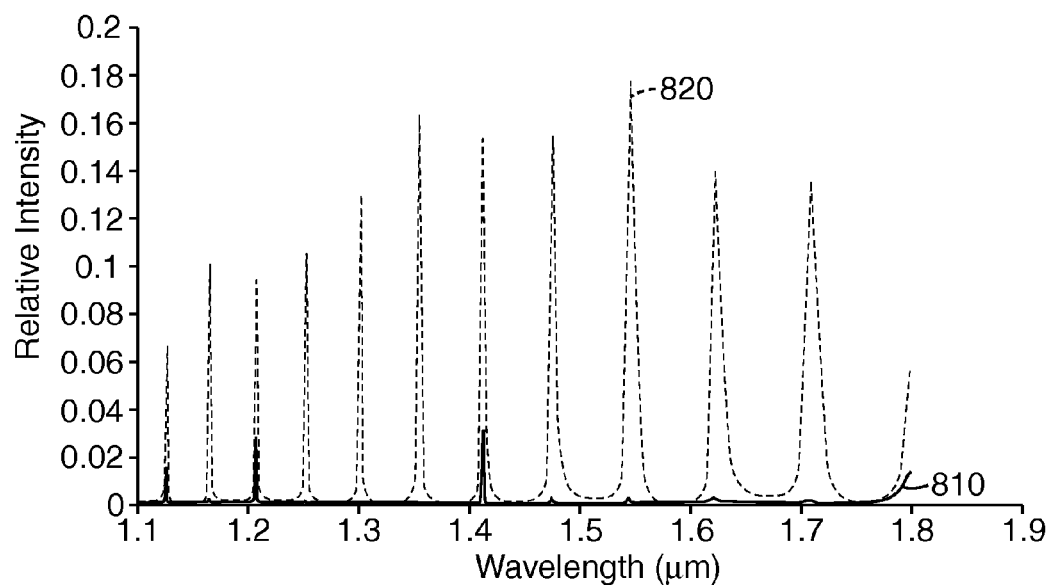
FIG. 8 is a plot of signal strength against wavelength, as detected at a drop two port of an optical system, with and without a silicon nanoparticle scattering center.

For this first example, the signal strength plotted against wavelength for the drop 2 port is illustrated in FIG. 8, where plot 810 represents the output for the ring with a water cladding only, and plot 820 represents the output for the ring with the silicon nanoparticle optically coupled to the ring. For the drop 2 port spectrum, the signal at a wavelength of 1.55 micron is almost 50 times higher with the nanoparticle than without it. Similar increases in intensity were present at many other resonant wavelengths suggesting the broadband nature of this technique. This demonstrates that the wavelength of the light source is selectable to obtain the largest signal enhancement when conducting sensing methods involving a scattering center.

Figure 9:
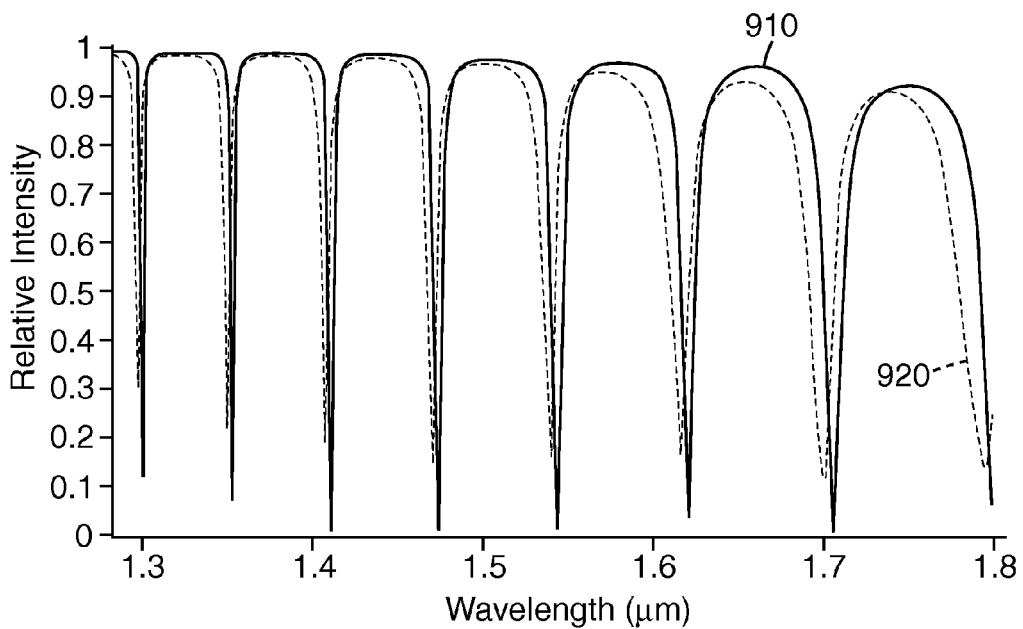
FIG. 9 is a plot of signal strength against wavelength, as detected at a through port of an optical system, with and without a gold nanoparticle scattering center.

A second example demonstrates the effect of a gold nanoparticle attached to a ring resonator with two bus waveguides, where the gold particle has a diameter of 80 nanometers and an index of refraction of 0.54+9.58 i near 1550 nanometers. The signal strength plotted against wavelength for the through port is illustrated in FIG. 9, where plot 910 represents the output for the ring with a water cladding only, and plot 920 represents the output for the ring with the gold nanoparticle in optical communication. For the through port spectrum, a peak shift of about 4 nanometers occurs at a wavelength of 1.55 microns.

Figure 10:
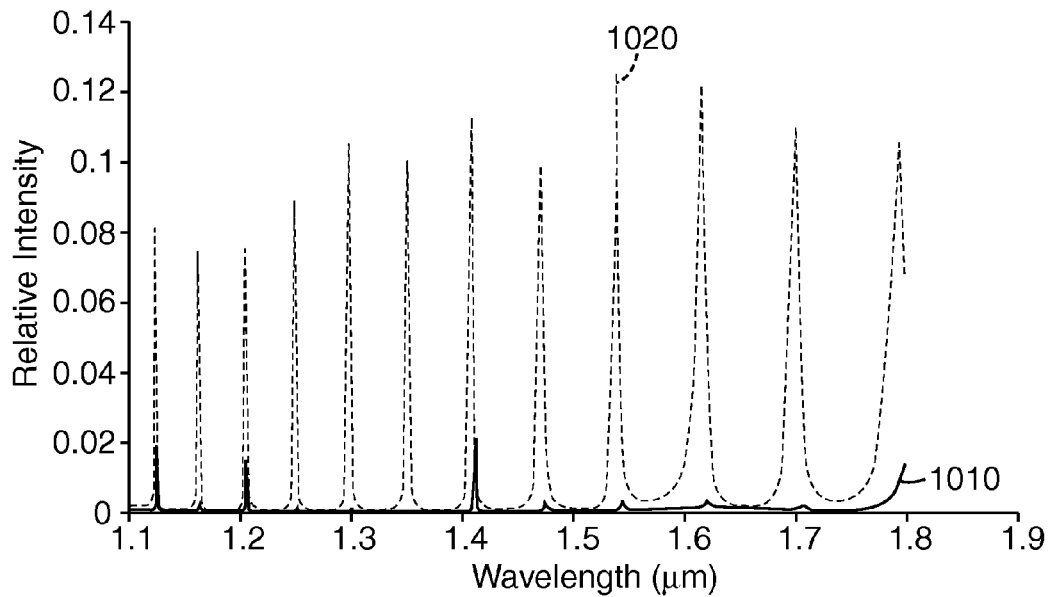
FIG. 10 is a plot of signal strength against wavelength, as detected at a drop two port of an optical system, with and without a gold nanoparticle scattering center.

For this second example, the signal strength plotted against wavelength for the drop 2 port is illustrated in FIG. 10, where plot 1010 represents the output for the ring with a water cladding only, and plot 1020 represents the output for the ring with the gold particle in optical communication. For the drop 2 port spectrum, the signal at a wavelength of 1.55 micron is much higher with the gold particle than without it. Gold has a small real refractive index and a very large imaginary refractive index (representative of absorption of the material) for visible to infrared wavelengths. Accordingly, in some cases, gold coated particles or gold particles can lead to a larger resonance wavelength shift at the through port and a significant signal enhancement at the drop 2 port.

Figure 11:
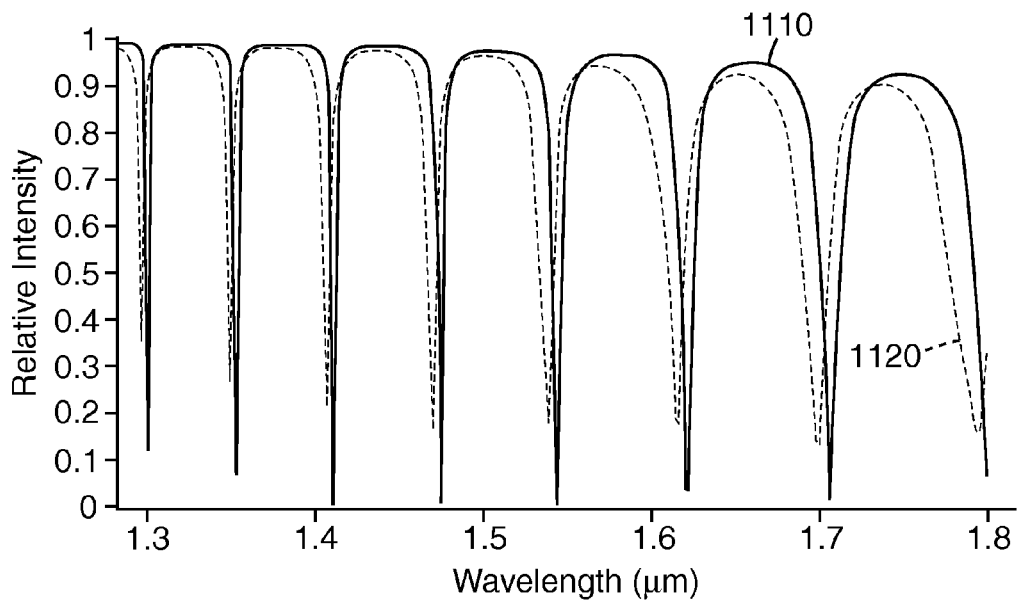
FIG. 11 is a plot of signal strength against wavelength, as detected at a through port of an optical system, with and without a aluminum nanoparticle scattering center.

A third example demonstrates the effect of an aluminum nanoparticle attached to a ring resonator with two bus waveguides, where the aluminum particle has a diameter of 80 nanometers and an index of refraction of 1.44+16.0 i near 1550 nanometers. The signal strength plotted against wavelength for the through port is illustrated in FIG. 11, where plot 1110 represents the output for the ring with a water cladding only, and plot 1120 represents the output for the ring with the aluminum nanoparticle in optical communication with the disk resonator. For the through port spectrum, a peak shift of about 5 nanometers occurs at a wavelength of 1.55 microns.

Figure 12:
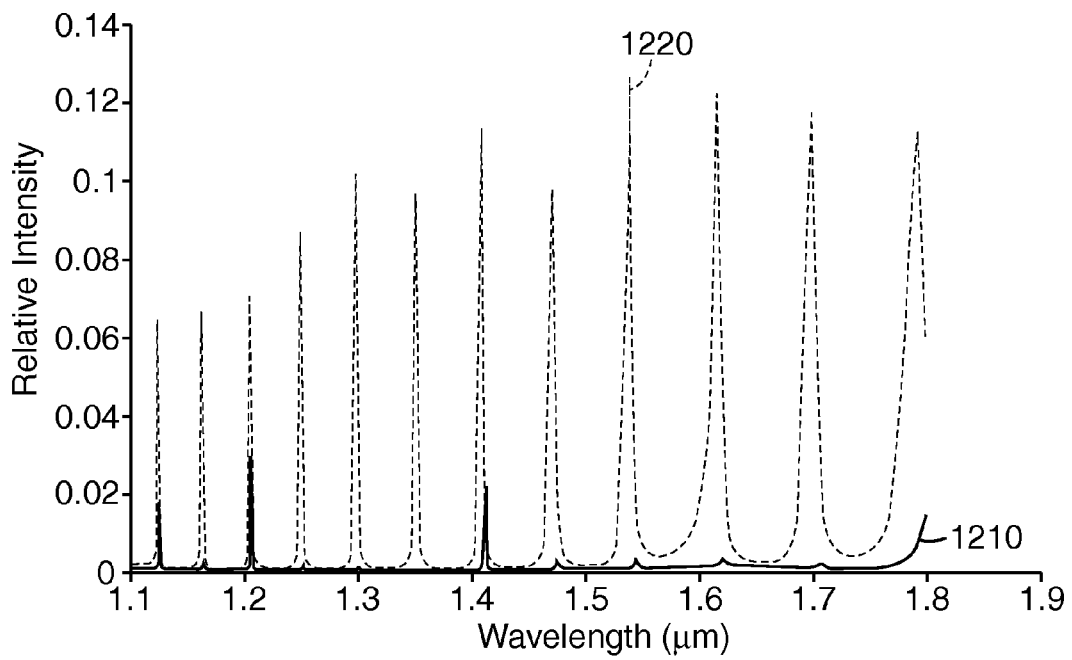
FIG. 12 is a plot of signal strength against wavelength, as detected at a drop two port of an optical system, with and without a aluminum nanoparticle scattering center.

For this third example, the intensity plotted against wavelength for the drop 2 port is illustrated in FIG. 12, where plot 1210 represents the output for the ring with a water cladding only, and plot 1220 represents the output for the ring with the aluminum particle in optical communication with the disk resonator. For the drop 2 port spectrum, the signal strength at a wavelength of 1.55 micron is much higher with the aluminum particle than without it. For aluminum, the real part of the refractive index is fairly high and aluminum has a large imaginary part of the refractive index (absorption). These properties can lead to a larger resonance wavelength shift at the through port and a larger signal enhancement at the drop 2 port. In addition, spectral peak broadening can be observed at the resonance wavelengths.

Some advantages associated with the disclosed devices are illustrated by the following example. The particular materials, amounts and dimensions recited in this example, as well as other conditions and details, should not be construed to unduly limit the present invention. An optical system similar to the device of FIG. 13 was fabricated. First, a 3 micron thick borophosphosilicate glass (BPSG) lower cladding layer with a refractive index of 1.46 was deposited on a 0.75 mm silicon (100 orientation) substrate using plasma enhanced chemical vapor deposition (PECVD). Next, the sample was heated and allowed to reflow at 1080° C. for about four hours. Next, a 250 nanometer thick SiN layer was deposited on the BPSDG lower cladding using PECVD. The deposited SiN layer formed the cores of two optical waveguides and had a refractive index of 2.0.

Next, the deposited SiN layer was patterned using conventional photolithography techniques and reactive ion etching (RIE) to produce ridge-shaped first and second bus waveguides. The etch depth for each waveguide was about 130 nanometers. The core of each waveguide was about 1.5 microns wide. Next, the bus waveguides were embedded by coating the waveguides with a 100 nanometer thick $SiO_2$ layer using PECVD. The $SiO_2$ layer had a refractive index of about 1.46.

Next, to form a microresonator, a 250 nanometer thick SiN layer having a refractive index of 2.0 was deposited on the $SiO_2$ layer using PECVD. The deposited SiN layer was formed into a 30 micron diameter disk using conventional photolithography techniques and reactive ion etching (RIE). The central axis of each bus waveguide was nominally lined up with the disk perimeter. The optical coupling between each waveguide and the microresonator was achieved by vertical evanescent coupling.

A scattering center was simulated by using a portable atomic force microscope (AFM) (model MOBILE S, available from Nanosurf, Liestal, Switzerland) to place a 10 micron silicon AFM probe tip (Model SICON A, available from Applied NanoStructures, Santa Clara, Calif.) within the optical field of the microresonator.

Light was launched into the first bus waveguide using a high-powered erbium-doped fiber amplifier (EDFA) light source (Model NP 3000 PS, available from Nuphoton technologies, Murrieta, Calif.) with spontaneous emission within a wavelength range of about 1540 nanometers to about 1575 nanommeters.

An optical splitter was placed near the drop 2 port of the optical system to allow both an optical spectrum analyzer (Model HP86142A available from Hewlett-Packard, Palo Alto, Calif.) and a broadband power meter (Model HP81532A, also available from Hewlett-Packard) to monitor the output at the drop 2 port.

Figure 15:
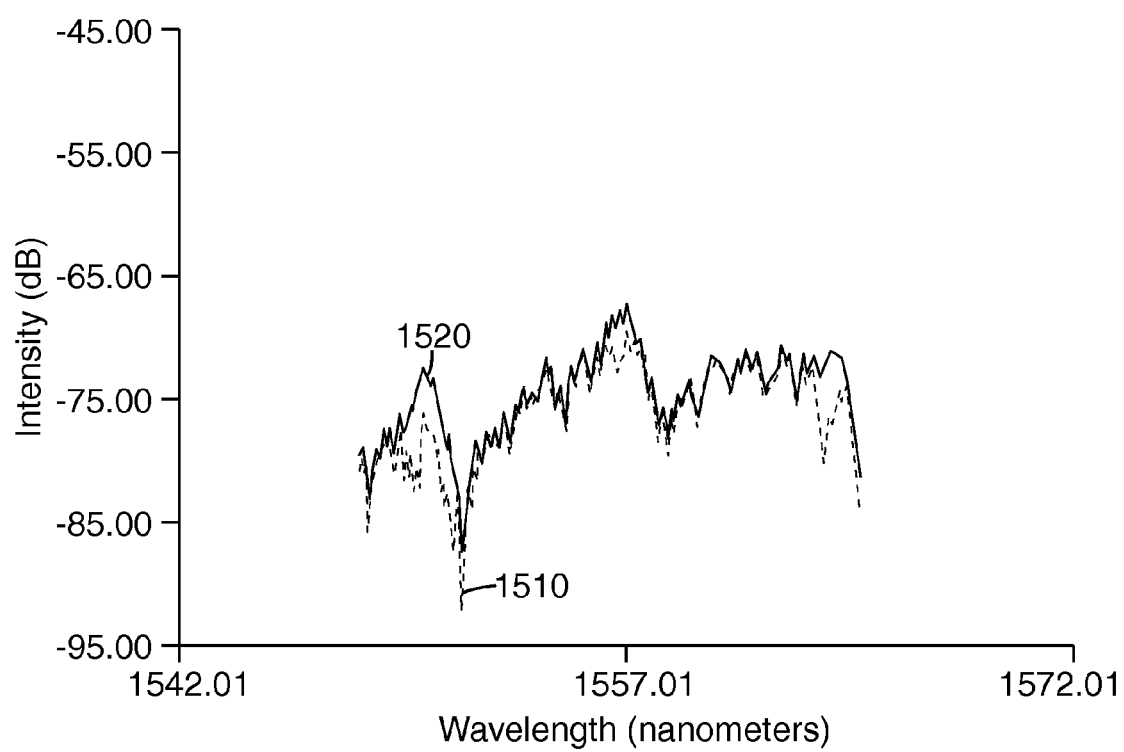
FIG. 15 is a plot of signal strength against wavelength, as detected at a drop two port of an optical system, with and without a scattering center.

The results are shown in FIG. 15. Curve 1510 is the output spectrum at the drop 2 port with the probe tip well outside the optical field of the disk microresonator (tip up). Curve 1520 shows the spectrum of the output light with the probe tip well within the optical field of the microresonator (tip down). Each curve has three resonances at approximately 1550 nm, 1557 nm, and 1564 nm. The presence of output light 1510 in the absence of a scattering center is believed to be due to surface roughness caused during the etching process resulting in optical scattering between the modes of the microresonator.

The total output power at the drop 2 port with the tip down was about 1.5 dB greater than the output power with the tip up. The increase was due to the presence of the probe tip acting as a scattering center.

The optical sensing systems of the present invention can be readily reproduced, easily handled, can maintain a high cavity Q-factor and can be readily aligned to a coupling waveguide. In some cases, the microcavity resonator and the waveguide can be integrated onto a same substrate. The disclosed embodiments permit the use of an inexpensive broadband light source such as a low cost light emitting diode (LED) in place of an expensive narrowband light source without sacrificing system sensitivity. The present invention also provides for the use of a broadband detector in place of an expensive spectroscopic detector with little or no loss of detection sensitivity.

The application also discloses sensing systems with enhanced sensitivity such as a larger wavelength shift or a stronger optical scattering between different modes. The enhanced sensitivity can allow the detection of, for example, a single analyte.

There is a need for optical sensing systems using microresonators that are easy to fabricate, produce larger spectral shifts upon exposure to analytes and can use less expensive light sources than a narrow-linewidth tunable laser.

Accordingly, the present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

We claim:

1. An optical sensing system comprising:
   a first bus waveguide, the first bus waveguide comprising an input port that is in optical communication with a light source;
   a second bus waveguide comprising a drop two port;
   a microresonator optically coupled to the first and second bus waveguides;
   an optical scattering center configured for alteration of a strength of optical coupling between the optical scattering center and the microresonator; and
   a detector in optical communication with the drop two port, wherein the optical sensing system is configured so that, in the absence of a scattering center optically coupled to the microresonator, light launched at the input port couples to a first guided optical mode of the microresonator and the first guided optical mode primarily does not couple to the drop two port.

2. The system of claim 1 wherein the microresonator is selected from a disk microresonator, a ring microresonator, a toroidal microresonator, and a racetrack microresonator.

3. The system of claim 1 wherein the scattering center comprises a particle.

4. The system of claim 3 wherein the particle is a nanoparticle.

5. The system of claim 4 wherein the nanoparticle is a metallic nanoparticle, a semiconductor nanoparticle, or a dielectric nanoparticle.

6. The system of claim 1 wherein the scattering center is a region of variable refractive index embedded in the core of the resonator.

7. The system of claim 1 wherein the second bus waveguide further comprises a drop port, wherein the optical sensing system is configured so that, in the absence of the scattering center optically coupled to the microresonator, the first guided optical mode of the microresonator couples to the drop port.

8. The system of claim 1 wherein the drop two port is primarily capable of optically coupling to a second guided optical mode of the microresonator and the detector is configured to detect the second guided optical mode.

9. The system of claim 8 wherein the optical sensing system is configured so that an alteration of the strength of optical coupling between the optical scattering center and the microresonator induces a change in optical scattering from the first resonant guided optical mode to the second guided optical mode.

10. The system of claim 9 wherein the optical sensing system is configured to detect the change in optical scattering at the detector at the drop two port.

11. The system of claim 1 wherein the microresonator and the first bus waveguide are integrated on a substrate.

12. The system of claim 11 wherein the light source is integrated on the substrate.

13. The system of claim 11 wherein the detector is integrated on the substrate.

14. The system of claim 1 wherein the microresonator is optically coupled to the first and second bus waveguides by a vertical coupling.

15. The system of claim 1, wherein the microresonator is optically coupled to the first and second bus waveguides by a lateral coupling.

16. The system of claim 1, wherein the microresonator is optically coupled to the first and second bus waveguides by evanescent coupling.

17. The system of claim 1, wherein the microresonator is optically coupled to the first and second bus waveguides by core coupling.

18. The system of claim 1, wherein the microresonator is optically coupled to the first and second bus waveguides via a multimode interference coupler.

19. An optical sensing system comprising:
    one or more bus waveguides, comprising a first bus waveguide, the first bus waveguide comprising an input port that is in optical communication with a light source that launches light into the first bus waveguide at the input port;
    a microresonator optically coupled to the one or more bus waveguides; and
    a detector in optical communication with the input port and receiving light that travels toward the input port in the first bus waveguide and exits the input port.

20. The system of claim 19 wherein the microresonator is selected from a disk microresonator, a ring microresonator, a toroidal microresonator, and a racetrack microresonator.

21. The system of claim 19 wherein the optical sensing system further comprises an optical scattering center configured for alteration of a strength of optical coupling between the optical scattering center and the microresonator.

22. The system of claim 19 wherein the microresonator and the first bus waveguide are integrated on a substrate.

23. The system of claim 22, wherein the light source is integrated on the substrate.

24. The system of claim 22 wherein the detector is integrated on the substrate.

25. The system of claim 19, further comprising an optical circulator in optical communication with the input port, wherein the optical circulator enables optical coupling of the second mode to the detector.

26. The system of claim 19, further comprising an optical splitter in optical communication with the input port, wherein the optical splitter enables optical coupling of the second mode to the detector.

27. An optical sensing system comprising:
- a first bus waveguide, the first bus waveguide comprising an input port that is in optical communication with a light source;
- a second bus waveguide comprising a drop port and a drop two port;
- a microresonator optically coupled to the first and second bus waveguides; and
- a detector in optical communication with the second bus waveguide, wherein:
    - (a) light launched at the input port is capable of coupling to:
        - i. a first guided optical mode of the microresonator; and
        - ii. a second guided optical mode of the microresonator that occurs primarily when a scattering center is in optical communication with the microresonator;
    - (b) the drop port is primarily capable of optically coupling to the first guided optical mode of the microresonator and is primarily not capable of coupling to the second guided optical mode;
    - (c) the drop two port is primarily capable of optically coupling to the second guided optical mode of the microresonator and is primarily not capable of coupling to the first guided optical mode,
    - (d) the detector is in optical communication with the drop two port.

28. The system of claim 27 wherein the microresonator is selected from a disk microresonator, a ring microresonator, a toroidal microresonator, and a racetrack microresonator.

29. The system of claim 27 wherein optical sensing system comprises a scattering center configured for alteration of a strength of optical coupling between the optical scattering center and the microresonator.

30. The system of claims 29 wherein the scattering center comprises a particle.

31. The system of claim 30 wherein the particle is a nanoparticle.

32. The system of claim 31 wherein the nanoparticle is a metallic nanoparticle, a semiconductor particle, or a dielectric nanoparticle.

33. The system of claim 29 wherein the scattering center is a region of variable refractive index embedded in a core of the resonator.

34. The system of claim 27 wherein the microresonator, the first bus waveguide, and the second bus waveguide are integrated on a substrate.

35. The system of claim 34 wherein the light source is integrated on the substrate.

36. The system of claim 34 wherein the detector is integrated on the substrate.

37. The system of claim 27 wherein the microresonator is optically coupled to the first and second bus waveguides by a vertical coupling.

38. The system of claim 27, wherein the microresonator is optically coupled to the first and second bus waveguides by a lateral coupling.

39. An optical sensing system comprising:
- one or more bus waveguides, comprising a first bus waveguide, the first bus waveguide comprising an input port that is in optical communication with a light source;
- a disk microresonator optically coupled to the one or more bus waveguides, the disk microresonator defining a center location; and
- a detector in optical communication with the disk microresonator and located at the center location of the disk microresonator.

40. The system of claim 39 wherein the microresonator, the first bus waveguide, the light source, and the detector are integrated on a substrate.

41. The system of claim 40, wherein the light source is hybridly integrated on the substrate.

42. The system of claim 40, wherein the microresonator, the first bus waveguide, and the detector are monolithically integrated on the substrate.

43. The system of claim 39, wherein the optical sensing system further comprises an optical scattering center configured for alteration of a strength of optical coupling between the optical scattering center and the microresonator.

44. The system of claim 43 wherein the scattering center comprises a particle.

45. The system of claim 44 wherein the particle is a nanoparticle.

46. The system of claim 45 wherein the nanoparticle is a metallic nanoparticle, a semiconductor nanoparticle, or a dielectric nanoparticle.

47. The system of claim 43 wherein the scattering center is a region of variable refractive index embedded in a core of the resonator.

* * * * *

UNITED STATES PATENT AND TRADEMARK OFFICE
CERTIFICATE OF CORRECTION

PATENT NO.        : 7,903,240 B2                                        Page 1 of 1
APPLICATION NO.   : 11/565920
DATED             : March 8, 2011
INVENTOR(S)       : Smith et al.

It is certified that error appears in the above-identified patent and that said Letters Patent is hereby corrected as shown below:

Column 16,

Line 50, Delete "nanommeters." and insert -- nanometers. --, therefor.

Signed and Sealed this
Third Day of May, 2011

David J. Kappos
*Director of the United States Patent and Trademark Office*